(12) United States Patent
Pelzer et al.

(10) Patent No.: US 12,326,550 B2
(45) Date of Patent: Jun. 10, 2025

(54) DEVICE FOR HOLDING SPECIMENS IN A MICROSCOPE

(71) Applicant: LEICA MICROSYSTEMS CMS GMBH, Wetzlar (DE)

(72) Inventors: Patric Pelzer, Wetzlar (DE); Christian Schumann, Lich (DE)

(73) Assignee: LEICA MICROSYSTEMS CMS GMBH, Wetzlar (DE)

( * ) Notice: Subject to any disclaimer, the term of this patent is extended or adjusted under 35 U.S.C. 154(b) by 910 days.

(21) Appl. No.: 17/594,181

(22) PCT Filed: Apr. 8, 2020

(86) PCT No.: PCT/EP2020/060034
§ 371 (c)(1),
(2) Date: Oct. 6, 2021

(87) PCT Pub. No.: WO2020/208081
PCT Pub. Date: Oct. 15, 2020

(65) Prior Publication Data
US 2022/0171176 A1    Jun. 2, 2022

(30) Foreign Application Priority Data

Apr. 8, 2019   (DE) .................... 10 2019 109 207.8

(51) Int. Cl.
*G02B 21/34*   (2006.01)
*B01L 3/00*   (2006.01)

(52) U.S. Cl.
CPC ............ *G02B 21/34* (2013.01); *B01L 3/5085* (2013.01); *B01L 2200/025* (2013.01);
(Continued)

(58) Field of Classification Search
CPC ....... B01L 2200/025; B01L 2200/0689; B01L 2200/12; B01L 2300/0609;
(Continued)

(56) References Cited

U.S. PATENT DOCUMENTS 4,659,222 A    4/1987  Ekholm
4,682,891 A    7/1987  De Macario et al.
(Continued)

FOREIGN PATENT DOCUMENTS

CN    201459767 U    5/2010
CN    105378537 A    3/2016
(Continued)

*Primary Examiner* — Jennifer Wecker
(74) *Attorney, Agent, or Firm* — LEYDIG, VOIT & MAYER, LTD.

(57) ABSTRACT

A device for receiving samples in a microscope is provided. The device comprises a microtiter plate. The microtiter plate comprises an inner part with cavities for the samples and with an optically transparent bottom plate, which seals the cavities underneath and a frame which defines a supporting surface and is configured to hold the inner part at least in a first position. The bottom plate is arranged above the supporting surface in the first position of the inner part. The inner part is movable relative to the frame along a direction (A) perpendicular to the supporting surface.

14 Claims, 9 Drawing Sheets

(52) U.S. Cl.
 CPC ... *B01L 2200/0689* (2013.01); *B01L 2200/12* (2013.01); *B01L 2300/0609* (2013.01); *B01L 2300/0829* (2013.01); *B01L 2300/168* (2013.01)

(58) Field of Classification Search
 CPC ..... B01L 2300/0829; B01L 2300/0851; B01L 2300/168; B01L 3/5085; C12M 23/12; C12M 41/36; G02B 21/34
 See application file for complete search history.

(56) References Cited

U.S. PATENT DOCUMENTS

| | | | |
|---|---|---|---|
| 2003/0184745 | A1 | 10/2003 | Deppe et al. |
| 2005/0142033 | A1* | 6/2005 | Glezer ................. B01L 3/5085 422/400 |
| 2008/0175757 | A1 | 7/2008 | Powell |
| 2008/0287307 | A1* | 11/2008 | Adrien ................. B01L 3/5085 506/7 |
| 2009/0047180 | A1 | 2/2009 | Kawahara |
| 2016/0170195 | A1 | 6/2016 | Siebenmorgen et al. |
| 2016/0214114 | A1* | 7/2016 | Tan ................. G01N 35/00029 |
| 2018/0164569 | A1 | 6/2018 | Brinkman et al. |
| 2020/0101455 | A1* | 4/2020 | Veiseh ................. B01L 3/5085 |

FOREIGN PATENT DOCUMENTS

| | | | |
|---|---|---|---|
| DE | 100 02 666 A1 | 8/2001 | |
| DE | 202007003536 U1 | 6/2007 | |
| EP | 0 135 502 A1 | 4/1985 | |
| EP | 1 945 359 B1 | 6/2014 | |
| EP | 2 809 443 B1 | 7/2018 | |
| JP | H09-281106 A | 10/1997 | |
| JP | 2006145393 A | 6/2006 | |
| JP | 2008267842 A | 11/2008 | |
| JP | 2008267950 A | 11/2008 | |
| WO | WO 8402775 A1 | 7/1984 | |
| WO | WO-9961152 A1 * | 12/1999 | ............ B01L 3/5085 |
| WO | WO 02/18052 A1 | 3/2002 | |

* cited by examiner

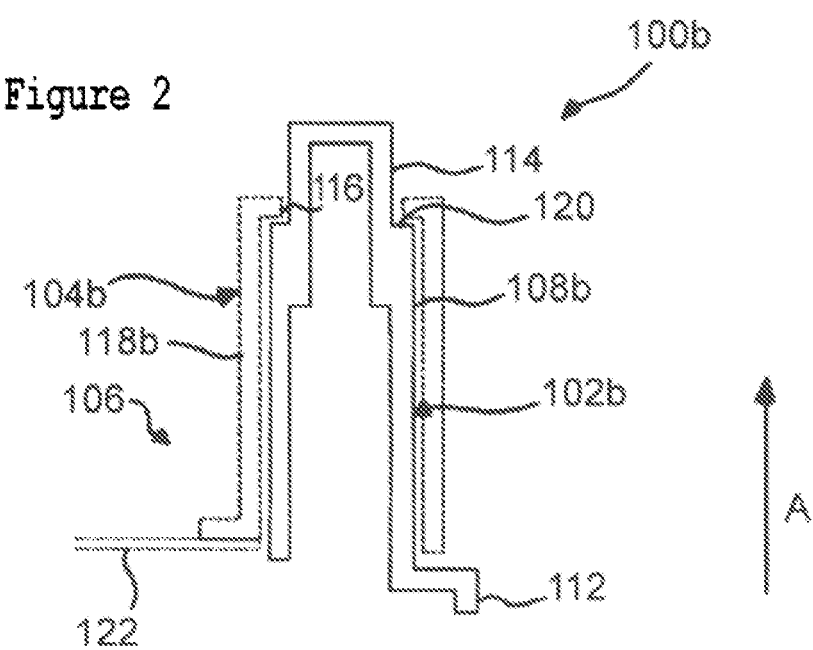

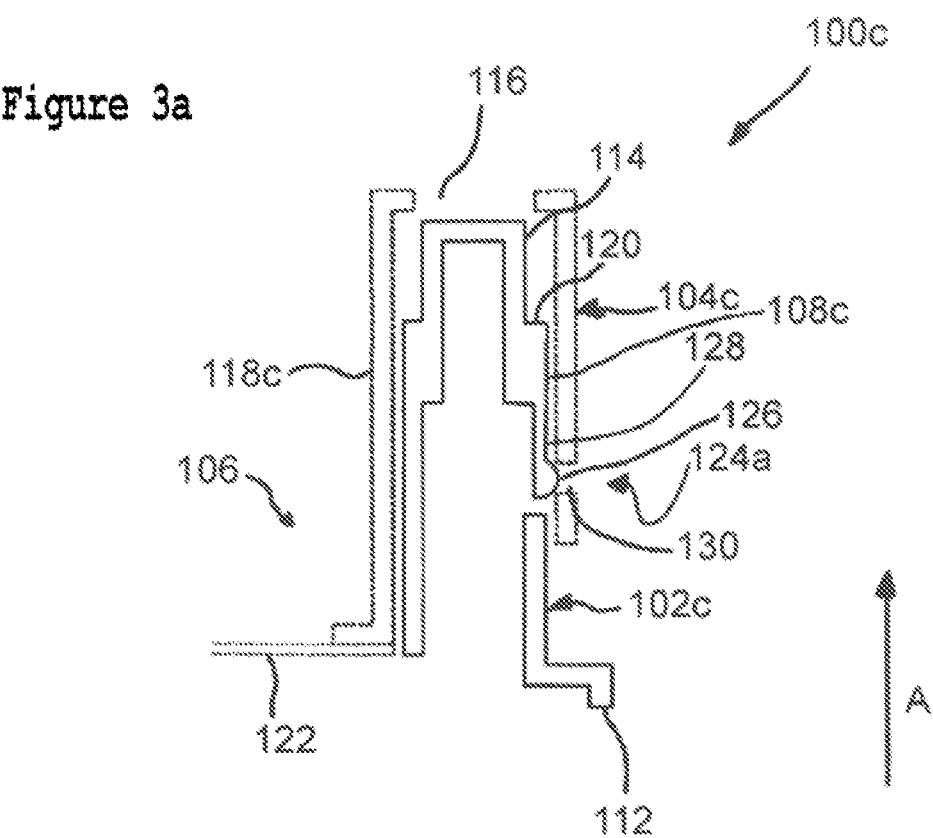

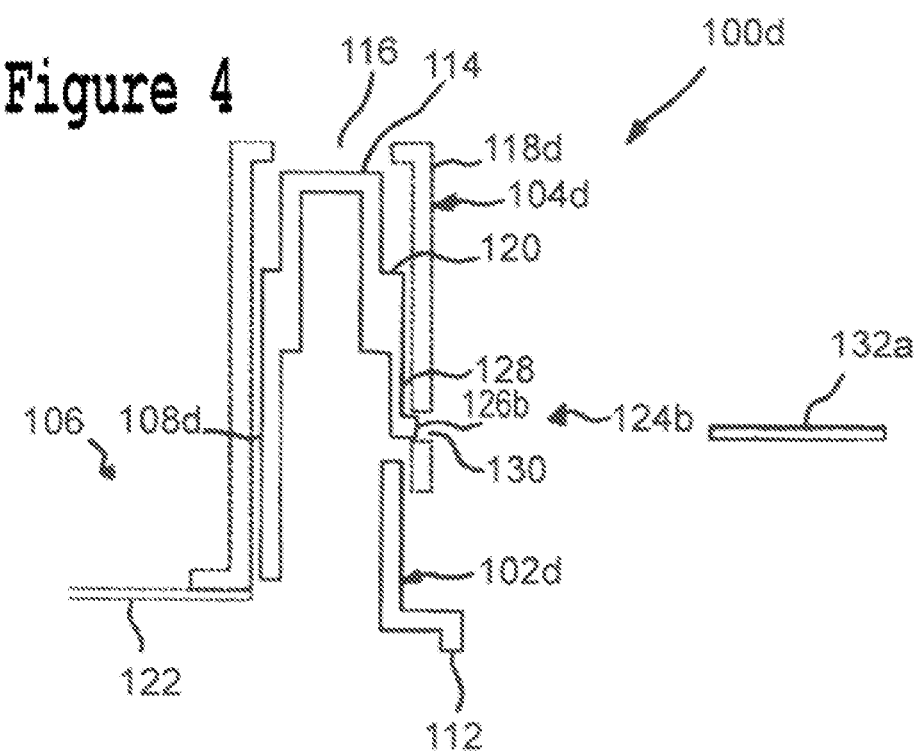

DEVICE FOR HOLDING SPECIMENS IN A MICROSCOPE

CROSS-REFERENCE TO PRIOR APPLICATIONS

This application is a U.S. National Phase application under 35 U.S.C. § 371 of International Application No. PCT/EP2020/060034, filed on Apr. 8, 2020, and claims benefit to German Patent Application No. DE 10 2019 109 207.8, filed on Apr. 8, 2019. The International Application was published in German on Oct. 15, 2020 as WO 2020/208081 under PCT Article 21(2).

FIELD

The invention relates to a device for receiving samples in a microscope.

BACKGROUND

In the field of light microscopy, it is necessary to examine a plurality of samples within a short time by means of a microscope. For this purpose, so-called microtiter plates are known from the prior art. These consist of cavities, also known as wells, which are arranged in the form of a grid in a frame. In order to examine the sample by means of an inverted microscope or transmitted-light microscope, the cavities are sealed underneath by an optically transparent bottom. The dimensions of microtiter plates are standardized by the Society for Laboratory Automation and Screening. The standard may be found at http://www.slas.org/resources/information/industry-standards/.

Particularly in a microscope with an objective that has a large optical flux, i.e. a large aperture angle or a high numerical aperture, and a moderate working distance, the frame of the microtiter plate constitutes a mechanical obstacle. In particular, the part of the objective facing toward the sample may collide with the frame of the microtiter plate. This prevents the outer cavities, i.e. those arranged close to the edge, being usable for sample examination. On the other hand, it is not possible simply to omit the frame since it forms a supporting surface for the microtiter plate. If the microtiter plate were to lie on the optically transparent bottom, the latter would become scratched and make observations of the samples arranged in the cavities difficult.

SUMMARY

In an embodiment, the present invention provides a device for receiving samples in a microscope. The device comprises a microtiter plate, and the microtiter plate comprises: an inner part with cavities for the samples and with an optically transparent bottom plate, which seals the cavities underneath, and a frame which defines a supporting surface and is configured to hold the inner part at least in a first position, wherein the bottom plate is arranged above the supporting surface in the first position of the inner part, and the inner part is movable relative to the frame along a direction perpendicular to the supporting surface.

BRIEF DESCRIPTION OF THE DRAWINGS

The present invention will be described in even greater detail below based on the exemplary figures. The invention is not limited to the exemplary embodiments. Other features and advantages of various embodiments of the present invention will become apparent by reading the following detailed description with reference to the attached drawings which illustrate the following:

FIG. 1b shows a perspective representation of a frame of the microtiter plate of the device for receiving samples in the microscope according to the embodiment of FIG. 1a;

FIG. 1c shows a perspective representation of an inner part of the microtiter plate of the device for receiving samples in the microscope according to the embodiment of FIG. 1a;

FIG. 2 shows a sectional representation of the microtiter plate according to one embodiment in an assembled state;

FIG. 3a shows a sectional representation of a locking device of the microtiter plate according to an embodiment in which the inner part is held in a first position;

FIG. 4 shows a sectional representation of the locking device of the microtiter plate according to an alternative embodiment;

DETAILED DESCRIPTION

Figure 1A:
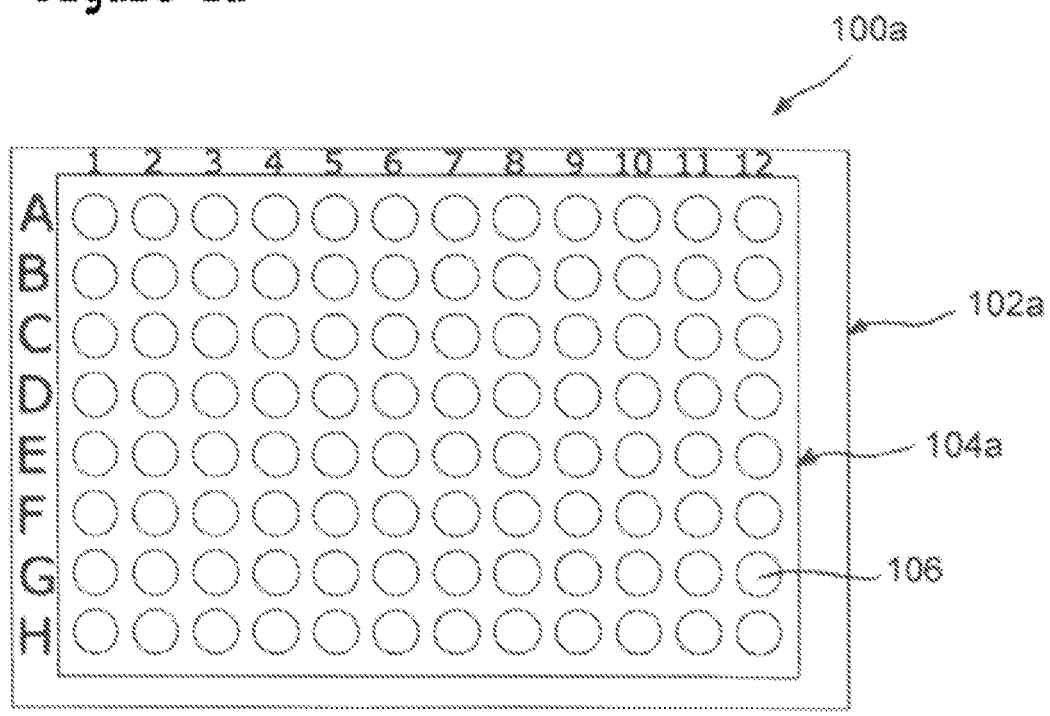
FIG. 1a shows a plan view of a microtiter plate of a device for receiving samples in a microscope according to one embodiment.

In an embodiment, the present application provides a device for receiving samples in a microscope, which allows examination of samples arranged in cavities of a microtiter plate by means of a microscope without a collision taking place between the device and an objective of the microscope.

The device comprises a microtiter plate with a frame and an inner part, which can be fitted into the frame. The inner part comprises the cavities, which are sealed underneath by the optically transparent bottom plate. In the present application, underneath is intended to mean in the direction of gravity. This means in particular that when the inner part is arranged in the first position, the bottom plate is respectively arranged at the end of the cavities which points in the direction of the supporting surface. When the inner part is held in the first position, i.e. the inner part is fitted into the frame, the bottom plate is arranged above the supporting surface of the frame. This prevents scratching of the bottom plate. In order to carry out an examination by means of the microscope, the inner part may be removed from the frame. The removed inner part may be introduced into the microscope, so that an examination of the samples arranged in the cavities by means of the microscope is made possible without a collision taking place between the device and an objective of the microscope.

In one preferred embodiment, the microtiter plate has a locking device, which is configured to connect the inner part and the frame releasably to one another. When the inner part and the frame are connected to one another, the microtiter plate may be used in any laboratory instrument intended for the use of microtiter plates. This increases the flexibility of the device. Preferably, the microtiter plate comprises at least three locking devices of the aforementioned type. In this way, the inner part is held in the first position at three bearing points. These three bearing points define a plane which is preferably parallel to the focal plane of the objective. The effect achieved by this is that the optically transparent bottom plate is parallel to the focal plane of the objective. This prevents image errors induced by tilting of the bottom plate in relation to the focal plane.

In a further preferred embodiment, the locking device has latching element, which is connected to the frame by means of an articulation, in particular a flexure bearing, and is configured to latch in a slot of the inner part and thus connect the inner part and the frame releasably to one another. A locking device that is particularly simple mechanically is formed in this way. In particular, the latching element may be formed by a spherical projection on the flexure bearing. This allows locking and/or unlocking by sliding.

In a further preferred embodiment, the device comprises an unlocking device with a pin which is configured to be guided through the slot of the inner part in order to push the latching element of the locking device out from the slot in such a way that the connection between the inner part and the frame is released. This prevents inadvertent release of the connection between the inner part and the frame. Furthermore, the release of the inner part from the frame may be automated easily by means of the pin. In particular, the unlocking device has a motorized drive for actuating the pin.

In one advantageous embodiment, the device comprises an unlocking device which is configured to release the connection between the inner part and the frame by pressing from above on the inner part. This allows simple actuation of the unlocking device by an operator, so that the device can be used more efficiently. The unlocking device may, in particular, comprise a lever mechanism.

In one advantageous embodiment, the device comprises a microscope stage insert with a guide element for guiding the microtiter plate, the guide element being configured to push the latching element of the locking device out from the slot during guiding of the microtiter plate, in such a way that the connection between the inner part and the frame is released. The inner part is therefore released from the frame when fitting the microtiter plate into the microscope and is movable along the direction perpendicular to the supporting surface. This allows particularly efficient use of the device.

In a further advantageous embodiment, the frame has an opening on its lower side, and the inner part can be moved in such a way that the bottom plate can be guided through the opening of the frame. In this way, the inner part can be positioned in such a way that the bottom plate is arranged below the supporting surface defined by the frame. Preferably, the inner part in this case protrudes through an opening in a microscope stage of the microscope when the supporting surface is lying on the microscope stage. The objective may thus be positioned close to the bottom plate in order to examine the samples, without the objective being able to collide with the frame of the microtiter plate. In particular, in this embodiment no further elements are required in order to arrange the inner part in the microscope.

It is advantageous for the frame to have a depth stop which is configured to hold the inner part in a second position, the inner part protruding through the opening of the frame in the second position, in such a way that the bottom plate of the inner part is arranged below the supporting surface. The depth stop prevents movement of the inner part relative to the frame. In particular, this also prevents movement of the bottom plate relative to the focal plane of the objective. Preferably, the frame has at least three depth stops, the respectively allocated bearing points of which—which means the points at which the inner part bears on the respective depth stop—define a plane that is parallel to the focal plane of the objective. This prevents image errors induced by tilting of the bottom plate in relation to the focal plane.

It is particularly advantageous for the device to comprise a microscope stage insert which is configured to hold the inner part in a second position, the inner part protruding through the opening of the frame in the second position, in such a way that the bottom plate of the inner part is arranged below the supporting surface. For this purpose, the microscope stage insert has for example a depth stop that positions the inner part in such a way that the bottom plate is parallel to the focal plane of the objective. Preferably, the microscope stage insert has three depth stops, the respectively allocated bearing points of which define a plane that is parallel to the focal plane of the objective.

In one preferred embodiment, the device comprises a microscope stage insert which is configured to hold the inner part in a third position, the inner part protruding through an opening of the microscope stage in the third position, in such a way that the bottom plate of the inner part is arranged below the microscope stage. In particular, the inner part is held by means of a depth stop. The microtiter plate may thus be moved relative to the objective in order to examine the samples, without the objective colliding with the frame of the microtiter plate.

In a further preferred embodiment, the frame has at least one guide element which is configured to guide the inner part perpendicularly with respect to the supporting surface. This ensures that the bottom plate remains parallel to the supporting surface and the focal plane of the objective even in the event of movement of the inner part.

In a further preferred embodiment, the device comprises two manipulators, the frame comprising engagement openings and the two manipulators being configured to engage through the engagement openings and hold the inner part. By means of the manipulators, the inner part may be positioned particularly precisely in order to prevent image errors induced by tilting of the bottom plate in relation to the focal plane.

In an embodiment, the cavities and the frame are configured as injection-molded plastic parts. In this way, the microtiter plate of the device may be produced particularly economically.

Elements that are the same or have the same effect are provided with the same references in the appended figures.

FIG. 1a shows a plan view of a microtiter plate 100a of a device for receiving samples in a microscope according to one embodiment.

Figure 1B:
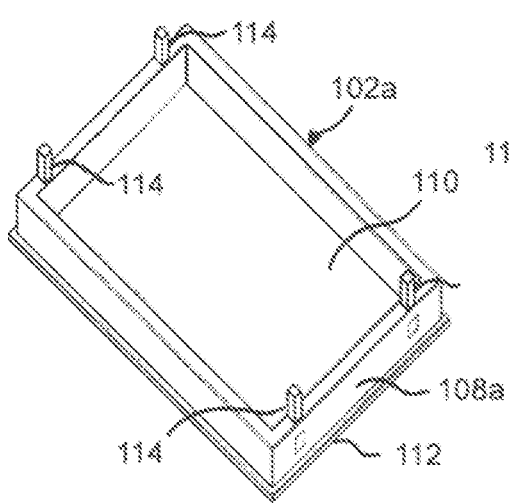
Figure 1C:
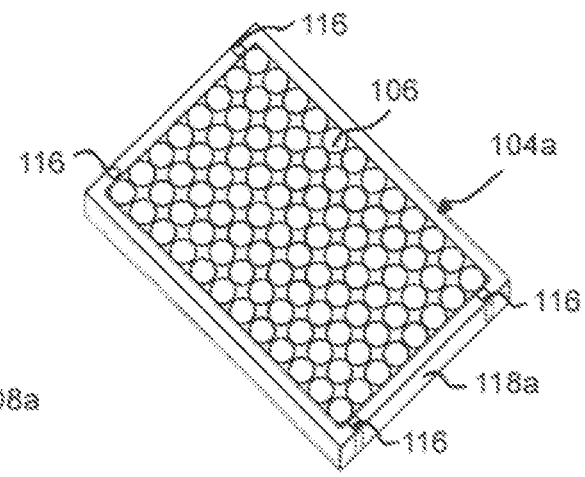

The microtiter plate 100a comprises a frame 102a and an inner part 104a, which are shown separately in FIGS. 1b and 1c, respectively. The inner part 104a has a multiplicity of cavities 106 for receiving samples. The cavities 106 are arranged in a grid and are respectively denoted from top to bottom by the letters A to H and from left to right by the numbers 1 to 12. In this way, each cavity 106 can be denoted uniquely by a combination of a letter and a number. The microtiter plate 100a shown in FIG. 1a has for example 96 cavities 106 arranged in a grid. As an alternative, other arrangements of cavities 106 may be envisioned, in particular those which are described by the standard issued by the Society for Laboratory Automation and Screening.

FIG. 1b shows a perspective representation of the frame 102a of the microtiter plate 100a of the device for receiving samples in the microscope according to the embodiment of FIG. 1a.

The frame 102a comprises a wall 108a, which encloses an opening 110 extending through the frame 102a in the vertical direction. The opening 110 is configured to receive the inner part 104a of the microtiter plate 100a. Arranged on the lower side of the wall 108a, there is a circumferential base 112 that defines a supporting surface of the frame 102a and therefore a supporting surface of the microtiter plate 100a. Arranged on the upper side of the frame 102a, there are four projections 114 that are configured to engage in holes 116 of the inner part 104a shown in FIG. 1c and thus prevent vertical slipping of the inner part 104a relative to the frame 102a. The projections 114 are part of a locking device which is described below with the aid of embodiments and FIGS. 3a to 5, where it is denoted by the references 124a to 124c.

FIG. 1c shows a perspective representation of the inner part 104a of the microtiter plate 100a of the device for receiving samples in the microscope according to the embodiment of FIG. 1a.

The inner part 104a comprises a structural element 118a, which comprises cavities 106 arranged in a grid. The holes 116 for the projections 114 of the frame 102a are arranged on the upper side of the structural element 118a.

FIG. 2 shows a sectional representation of the microtiter plate 100b according to one embodiment in an assembled state. The section extends perpendicularly to the longitudinal direction of the walls 108b, 118b of the frame 102b and of the inner part 104b.

FIG. 2 shows by way of example only the cavities 106 of the inner part 104b. In the embodiment shown, the cavity 106 is formed by a cylindrical recess of the structural element 118b of the inner part 104b, which extends in the direction A perpendicular to the supporting surface and the lower end of which is sealed by an optically transparent bottom plate 122. As an alternative, the cavities 106 may also be formed by rectangular recesses of the structural element 118b, in particular with rounded edges.

At the start of the projection 114, the frame 102b forms a supporting surface 120 on which the inner part 104b can bear. In this way, the inner part 104b can be held in a first position, in which the bottom plate 122 is arranged above the supporting surface formed by the base 112. The inner part 104b can be moved along the projection 114 in a direction A perpendicular to the supporting surface, in order to separate the inner part 104b from the frame 102b. The projection 114 therefore forms a guide element for guiding the inner part 104b.

FIG. 3a shows a sectional representation of the locking device 124a of the microtiter plate 100c according to one embodiment. In FIG. 3a, the inner part 104c is held in the first position.

The locking device 124a comprises a spherically shaped latching element 126a, which is connected to the frame 102c by means of a flexure bearing 128. The latching element 122a is configured to latch in a slot 130 of the structural element 118c of the inner part 104c and thus connect the inner part 104c and the frame 102c releasably to one another. The spherical shape of the latching element 126a allows sliding latching and unlatching of the latching element 126a in the slot 130 of the structural element 118c of the inner part 104c. In FIG. 3a, the latching element 126a is latched in the slot 130 and thereby holds the inner part 104c securely in the first position.

Figure 3B:
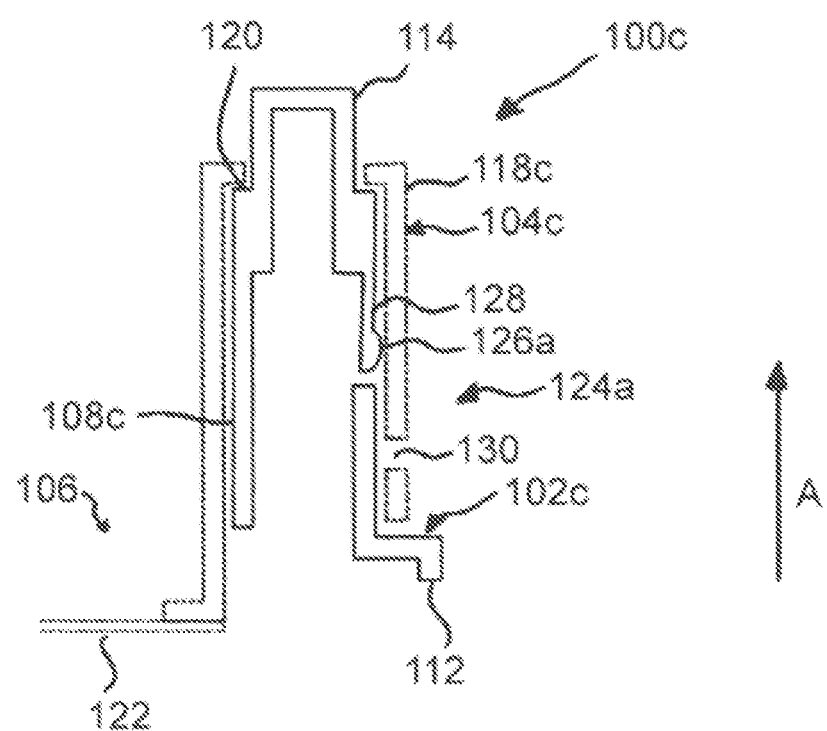
FIG. 3b shows a sectional representation of the locking device of the microtiter plate according to the embodiment of FIG. 3a, in which the inner part is held in a second position.

FIG. 3b shows a sectional representation of the locking device 124a of the microtiter plate 100c according to the embodiment of FIG. 3a. In FIG. 3b, the inner part 104c is held in a second position, in which the bottom plate 122 is arranged below the supporting surface so that the frame 102c does not constitute a mechanical obstacle for an objective of the microscope.

In FIG. 3b, the latching element 126a is not latched in the slot 130. Furthermore, the inner part 104c is displaced downward relative to the representation in FIG. 3a along the direction A perpendicular to the supporting surface. In FIG. 3b, the inner part 104c bears on the supporting surface 120 formed by the wall 108c of the frame 102c and is thereby held in the second position.

FIG. 4 is a sectional representation of the locking device 124b of the microtiter plate 100d according to an alternative embodiment. The locking device 124b according to FIG. 4 differs from the locking device 124a according to FIGS. 3a and 3b in that the latching element 126b is not spherically shaped. In this way, unlatching of the latching element 126b from the slot 130 of the structural element 118d of the inner part 104b in order to release the connection between the inner part 104d and the frame 102d is not possible by sliding. In order to release the connection between the inner part 104d and the frame 102d, a pin 132a is required. The pin 132a is configured to be guided through the slot 130 of the inner part 104c in order to push the latching element 126b of the locking device 124b out from the slot 130. The pin 132a therefore forms an unlocking device.

Figure 5:
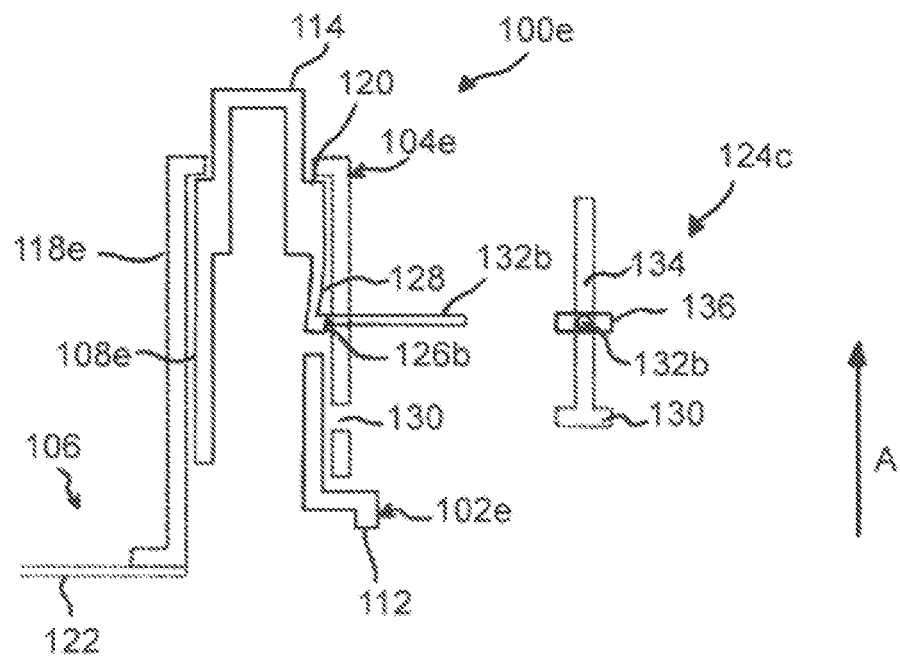
FIG. 5 shows a sectional representation of the locking device of the microtiter plate according to a further alternative embodiment.

FIG. 5 shows a sectional representation of the locking device 124c of the microtiter plate 100e according to a further alternative embodiment. The locking device 124c according to FIG. 5 differs from the locking device 124b according to FIG. 4 in that, in addition, a guide rail 134 that guides the pin 132b along the direction A perpendicular to the supporting surface is also arranged above the slot 130 of the inner part 104e. This prevents vertical slipping of the inner part 104e relative to the frame 102e. The projections 114 may therefore be omitted in the alternative embodiment. Furthermore, the pin 132b has a guide element 136 that prevents the pin 132b slipping out from the guide rail 134 while the pin 132b is being guided along the direction A perpendicular to the supporting surface. The shape of the guide element 136 furthermore prevents latching of the latching element 126b in the slot 130 of the structural element 118e of the inner part 104e.

Figure 6:
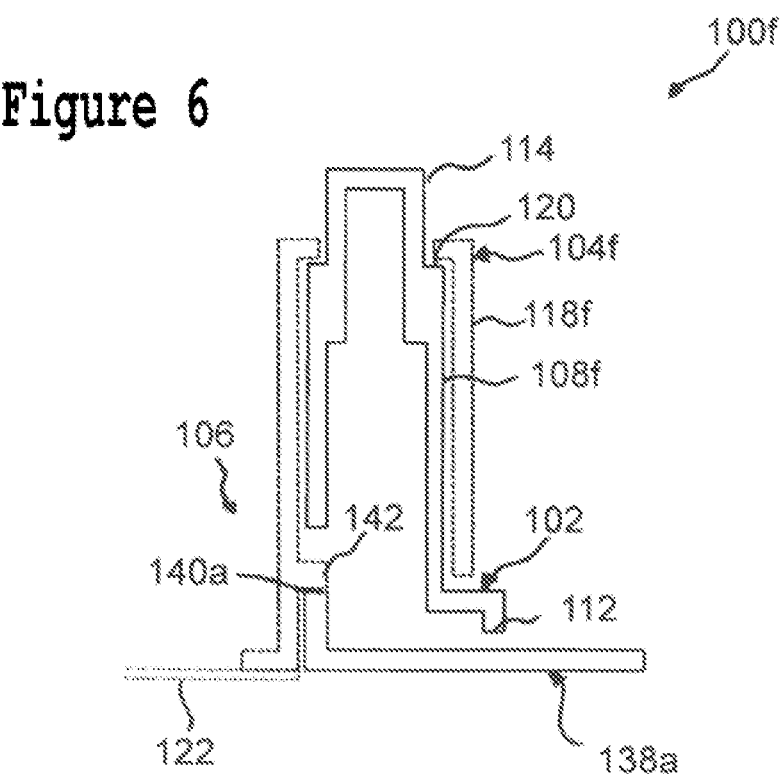
FIG. 6 shows a sectional representation of the device for receiving samples in the microscope according to an embodiment with a microscope stage insert.

FIG. 6 shows a sectional representation of the microtiter plate 100f according to an embodiment with a microscope stage insert 138a.

The microscope stage insert 138a has a depth stop 140a on which a projection 142, which is formed on the structural element 118f of the inner part 104f, can bear. When the projection 142 is bearing on the depth stop 140a, the inner part 104f is held in the second position. In the embodiment according to FIG. 6, the supporting surface 120 formed by the wall 108c of the frame 102c may be omitted. In particular, the embodiment according to FIG. 6 may advantageously be refined by elements of the locking device 124a to 124c according to FIGS. 3a, 3b, 4 and 5.

Figure 7:
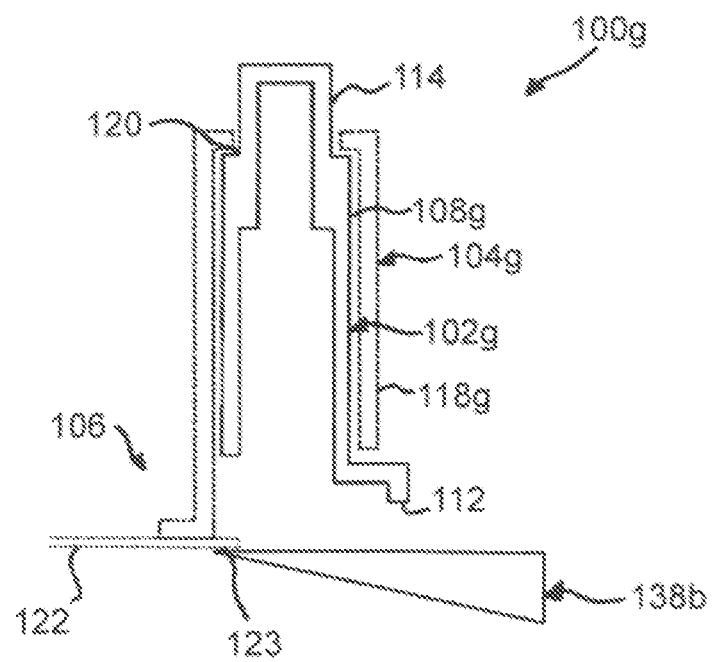
FIG. 7 shows a sectional representation of the device for receiving samples in the microscope according to an alternative embodiment with a microscope stage insert.

FIG. 7 shows a sectional representation of the device for receiving samples in the microscope according to an alternative embodiment with the microtiter plate 100g and the microscope stage insert 138b.

The microscope stage insert 138b has a depth stop 140b on which a projection 123 of the bottom plate 122 can bear. When the projection 123 is bearing on the depth stop 140b, the inner part 104f is held in a third position. In the third position, the inner part 104g protrudes through an opening of the microscope stage in such a way that the bottom plate 122 of the inner part 104g is arranged below the microscope stage. In this way, neither the microscope stage nor the frame 102g constitutes a mechanical obstacle for the objective of the microscope. The supporting surface 120 formed by the wall 108c of the frame 102c may also be omitted in the embodiment according to FIG. 7.

Various exemplary embodiments of the device for receiving samples in the microscope, which allows examination of the samples arranged in the cavities by means of the microscope without a collision taking place between the frame of the microtiter plate and the objective of the microscope, have been described with the aid of FIGS. 1a to 7.

Although some aspects have been described in connection with a device, it is clear that these aspects also represent a description of the corresponding method, a block or a device corresponding to a method step or a function of a method step. Similarly, aspects that have been described in connection with a method step also represent a description of a corresponding block or element or a property of a corresponding device. Some or all method steps may be embodied by (or by using) a hardware device, for example a processor, a microprocessor, a programmable or an electronic circuit. In some exemplary embodiments, one or more of the most important method steps may be embodied by such a device.

Depending on particular implementation requirements, exemplary embodiments of the invention may be implemented in hardware or software. The implementation may be carried out with a nonvolatile storage medium such as a digital storage media, for example a floppy disk, a DVD, a Blu-Ray, a CD, an ROM, a PROM and EPROM, an EEPROM or a FLASH memory, on which electronically readable control signals that interact (or can interact) with a programmable computer system in such a way that the respective method is carried out are stored. The digital storage medium may therefore be computer-readable.

Some exemplary embodiments according to the invention comprise a data carrier having electronically readable control signals that can interact with a programmable computer system so that one of the methods described here is carried out.

In general, exemplary embodiments of the present invention may be implemented as a computer program product having a program code, the program code being effective for carrying out one of the methods when the computer program product runs on a computer. The program code may, for example, be stored on a machine-readable carrier.

Further exemplary embodiments comprise the computer program for carrying out one of the methods described here, which is stored on a machine-readable carrier.

In other words, one exemplary embodiment of the present invention is therefore a computer program having a program code for carrying out one of the methods described here when the computer program runs on a computer.

A further exemplary embodiment of the present invention is therefore a storage medium (or a data carrier or a computer-readable medium) that comprises a computer program stored thereon for carrying out one of the methods described here when it is executed by a processor. The data carrier, the digital storage medium or the recorded medium are in general tangible and/or not transitionless. A further exemplary embodiment of the present invention is a device as described here that comprises a processor and the storage medium.

A further exemplary embodiment of the invention is therefore a data stream or a signal sequence that represents the computer program for carrying out one of the methods described here. The data stream or the signal sequence may for example be configured in such a way that they are transmitted via a data communication connection, for example via the Internet.

A further exemplary embodiment comprises a processing means, for example a computer or a programmable logic device, which is configured or adapted to carry out one of the methods described here.

A further exemplary embodiment comprises a computer on which the computer program for carrying out one of the methods described here is installed.

A further exemplary embodiment according to the invention comprises a device or a system that is configured to transmit (for example electronically or optically) a computer program for carrying out one of the methods described here to a receiver. The receiver may for example be a computer, a mobile device, a memory device or the like. The device or the system may, for example, comprise a file server for transmitting the computer program to the receiver.

In some exemplary embodiments, a programmable logic device (for example a field-programmable gate array, FPGA) may be used in order to carry out some or all functionalities of the methods described here. In some exemplary embodiments, a field-programmable gate array may interact with a microprocessor in order to carry out one of the methods described here. In general, the methods are preferably carried out by any hardware instrument.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below. Additionally, statements made herein characterizing the invention refer to an embodiment of the invention and not necessarily all embodiments.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

| List of References | |
|---|---|
| 100a-100g | microtiter plate |
| 102a-102g | frame |
| 104a-104g | inner part |

-continued

| List of References | |
|---|---|
| 106 | cavity |
| 108a-108g | wall |
| 110 | opening |
| 112 | base |
| 114 | projection |
| 116 | hole |
| 118a-118g | structural element |
| 120 | supporting surface |
| 122 | bottom plate |
| 123 | projection |
| 124a-124c | locking device |
| 126a, 126b | latching element |
| 128 | flexure bearing |
| 130 | slot |
| 132a, 132b | pin |
| 134 | guide rail |
| 136 | guide element |
| 138a, 138b | microscope stage insert |
| 140a, 140b | depth stop |
| 142 | projection |

The invention claimed is:

1. A device for receiving samples in a microscope, comprising:
a microtiter plate comprising:
an inner part with cavities for the samples and with an optically transparent bottom plate, which seals the cavities underneath, and
a frame which defines a supporting surface and is configured to hold the inner part at least in a first position and in a second position,
wherein the bottom plate is arranged above the supporting surface in the first position of the inner part,
wherein the inner part is movable relative to the frame along a direction perpendicular to the supporting surface, and
wherein the frame has a depth stop which is configured to hold the inner part in the second position, the inner part protruding through an opening on a lower side of the frame in the second position in such a way that the bottom plate of the inner part is arranged below the supporting surface.

2. The device according to claim 1, wherein the microtiter plate has a locking device, which is configured to connect the inner part and the frame releasably to one another.

3. The device according to claim 2, wherein the locking device has latching element, which is connected to the frame by an articulation and is configured to latch in a slot of the inner part and thus connect the inner part and the frame releasably to one another.

4. The device according to claim 3, further comprising an unlocking device with a pin which is configured to be guided through the slot of the inner part in order to push the latching element of the locking device out from the slot, in such a way that the connection between the inner part and the frame is released.

5. The device according to claim 4, wherein the unlocking device has a motorized drive for actuating the pin.

6. The device according to claim 2, further comprising an unlocking device which is configured to release the connection between the inner part and the frame by pressing from above on the inner part.

7. The device according to claim 2, further comprising a microscope stage insert with a guide element for guiding the microtiter plate, wherein the guide element is configured to push the latching element of the locking device out from the slot during guiding of the microtiter plate, in such a way that the connection between the inner part and the frame is released.

8. The device according to claim 1, wherein the inner part is movable in such a way that the bottom plate can be guided through the opening of the frame.

9. The device according to claim 1, further comprising a microscope stage insert, which is configured to hold the inner part in a third position, wherein the inner part protrudes through an opening of the microscope stage in the third position, in such a way that the bottom plate of the inner part is arranged below the microscope stage.

10. The device according to claim 1, wherein the frame has at least one guide element, which is configured to guide the inner part perpendicularly with respect to the supporting surface.

11. The device according to claim 1, further comprising two manipulators, wherein the frame comprises engagement openings and the two manipulators are configured to engage through the engagement openings and hold the inner part.

12. The device according to claim 1, wherein the cavities and the frame are configured as injection-molded plastic parts.

13. A device for receiving samples in a microscope, comprising:
a microtiter plate comprising:
an inner part with cavities for the samples and with an optically transparent bottom plate, which seals the cavities underneath,
a frame which defines a supporting surface and is configured to hold the inner part at least in a first position, and
a microscope stage insert, which is configured to hold the inner part in a second position,
wherein the bottom plate is arranged above the supporting surface in the first position of the inner part,
wherein the inner part is movable relative to the frame along a direction perpendicular to the supporting surface, and
wherein the inner part protrudes through an opening on a lower side of the frame in the second position in such a way that the bottom plate of the inner part is arranged below the supporting surface.

14. A device for receiving samples in a microscope, comprising:
a microtiter plate comprising:
an inner part with cavities for the samples and with an optically transparent bottom plate, which seals the cavities underneath,
a frame which defines a supporting surface and is configured to hold the inner part at least in a first position, and
a microscope stage insert, which is configured to hold the inner part in a third position, wherein the inner part protrudes through an opening of the microscope stage in the third position in such a way that the bottom plate of the inner part is arranged below the microscope stage,
wherein the bottom plate is arranged above the supporting surface in the first position of the inner part, and the inner part is movable relative to the frame along a direction perpendicular to the supporting surface.

* * * * *